(12) United States Patent
Sukovic et al.

(10) Patent No.: US 7,209,538 B2
(45) Date of Patent: Apr. 24, 2007

(54) INTRAOPERATIVE STEREO IMAGING SYSTEM

(75) Inventors: Predrag Sukovic, Birmingham, MI (US); Neal Clinthorne, Ann Arbor, MI (US); Nathaniel Bair, Ann Arbor, MI (US)

(73) Assignee: Xoran Technologies, Inc., Ann Arbor, MI (US)

( * ) Notice: Subject to any disclaimer, the term of this patent is extended or adjusted under 35 U.S.C. 154(b) by 6 days.

(21) Appl. No.: 10/914,494

(22) Filed: Aug. 9, 2004

(65) Prior Publication Data

US 2005/0053192 A1    Mar. 10, 2005

Related U.S. Application Data

(60) Provisional application No. 60/493,265, filed on Aug. 7, 2003.

(51) Int. Cl.
*A61B 6/02* (2006.01)
*H05G 1/02* (2006.01)

(52) U.S. Cl. .................. 378/42; 378/41; 378/189; 378/190; 378/197; 600/429

(58) Field of Classification Search .................. 378/5, 378/9, 41, 42, 92, 98.9, 190, 196–198, 205, 378/11, 25, 26, 181, 206, 19; 600/407, 424, 600/425, 429
See application file for complete search history.

(56) References Cited

U.S. PATENT DOCUMENTS

| | | | |
|---|---|---|---|
| 4,341,220 A | | 7/1982 | Perry |
| 4,349,740 A | * | 9/1982 | Grassmann et al. .......... 378/25 |
| 4,737,972 A | * | 4/1988 | Schoolman .................... 378/41 |
| 4,791,934 A | * | 12/1988 | Brunnett ...................... 600/429 |
| 5,078,140 A | * | 1/1992 | Kwoh .......................... 600/417 |
| 5,099,846 A | | 3/1992 | Hardy |
| 5,446,548 A | * | 8/1995 | Gerig et al. ................. 356/620 |
| 5,665,095 A | | 9/1997 | Jacobson |

(Continued)

FOREIGN PATENT DOCUMENTS

| | | |
|---|---|---|
| WO | WO 94/10908 | 5/1994 |
| WO | WO 00/64367 | 11/2000 |
| WO | WO 02/065931 A1 | 8/2002 |
| WO | WO 03/009768 A1 | 2/2003 |

*Primary Examiner*—Allen C. Ho
(74) *Attorney, Agent, or Firm*—Carlson, Gaskey & Olds

(57) ABSTRACT

A surgical imaging system includes spaced-apart first and second x-ray sources mounted above a patient support surface. An x-ray detector mounted below the patient support surface generates first x-ray images based upon x-rays from the first x-ray source and second x-ray images based upon x-rays from the second x-ray source. These first and second x-ray images are used to generate a stereofluoroscopic image via a stereo display for a surgeon performing image-guided surgery. The stereofluoroscopic imaging system may be used in conjunction with robotic surgery. A surgical robot operatively controls a surgical tool in an area between the first x-ray source and the x-ray detector, and between the second x-ray source and the x-ray detector. The system may optionally include a first video camera mounted proximate the first x-ray source and a second video camera mounted proximate the second x-ray source. The stereo display selectively displays the first and second video images or the first and second x-ray image, and dissolves between the sources to correlate an outer view with the fluoroscopic view.

13 Claims, 2 Drawing Sheets

U.S. PATENT DOCUMENTS

| | | | |
|---|---|---|---|
| 5,799,055 A * | 8/1998 | Peshkin et al. | 378/42 |
| 5,944,663 A * | 8/1999 | Kuth et al. | 600/411 |
| 5,951,475 A * | 9/1999 | Gueziec et al. | 600/425 |
| 6,052,611 A * | 4/2000 | Yanof et al. | 600/429 |
| 6,088,424 A * | 7/2000 | Postlethwaite et al. | 378/63 |
| 6,256,372 B1 * | 7/2001 | Aufrichtig et al. | 378/41 |
| 6,386,758 B2 * | 5/2002 | Loser | 378/205 |
| 6,400,979 B1 * | 6/2002 | Stoianovici et al. | 600/427 |
| 6,449,333 B1 * | 9/2002 | Yamasaki | 378/42 |
| 6,490,475 B1 * | 12/2002 | Seeley et al. | 600/426 |
| 6,763,083 B2 * | 7/2004 | Fernandez | 378/41 |
| 6,914,959 B2 * | 7/2005 | Bailey et al. | 378/65 |
| 7,008,373 B2 * | 3/2006 | Stoianovici et al. | 600/101 |
| 7,150,737 B2 * | 12/2006 | Purdy et al. | 604/506 |
| 2001/0029334 A1 | 10/2001 | Graumann et al. | |

* cited by examiner

INTRAOPERATIVE STEREO IMAGING SYSTEM

This application claims priority to U.S. Provisional Application Ser. No. 60/493,265 filed Aug. 7, 2003.

BACKGROUND OF THE INVENTION

Image guided surgery is becoming more common. Systems are utilized to take data gathered from pre-operative scans by MRI, CT scanners, ultrasounds, or the like. The data is used to generate a three-dimensional image to guide a surgeon during an operation. Often this includes some method for tracking an instrument location with respect to the image displayed by the system. Generally, the image is registered relative to locators attached to the patient. Then, the position and orientation of the surgical instruments is registered and tracked relative to the image and the patient so that the location and orientation of the instruments relative to the image is continuously displayed while the surgeon performs the surgery. However, the current image-guided surgery relies on a preoperative scan. Changes to the surgical area during surgery are not reflected in the image by which the surgeon navigates.

Fluoroscopy is used in some types of surgery to provide a continuously updated image of the surgical area. However, the two dimensional nature of the fluoroscopy may not provide sufficient information for surgical navigation.

SUMMARY OF THE INVENTION

A surgical imaging system according to one embodiment of the present invention includes spaced-apart first and second x-ray sources mounted above a patient support surface. An x-ray detector mounted below the patient support surface generates first x-ray images based upon x-rays from the first x-ray source and second x-ray images based upon x-rays from the second x-ray source. These first and second x-ray images are used to generate a stereofluoroscopic image via a stereo display for a surgeon performing image-guided surgery.

The stereofluoroscopic imaging system may be used in conjunction with robotic surgery. A surgical robot operatively controls a surgical tool in an area between the first x-ray source and the x-ray detector, and between the second x-ray source and the x-ray detector.

The system may optionally include a first video camera mounted proximate the first x-ray source and a second video camera mounted proximate the second x-ray source. The stereo display selectively displays the first and second video images or the first and second x-ray image, and dissolves between the sources to correlate an outer view with the fluoroscopic view.

BRIEF DESCRIPTION OF THE DRAWINGS

Other advantages of the present invention can be understood by reference to the following detailed description when considered in connection with the accompanying drawings wherein.

DETAILED DESCRIPTION OF THE PREFERRED EMBODIMENTS

Figure 1:
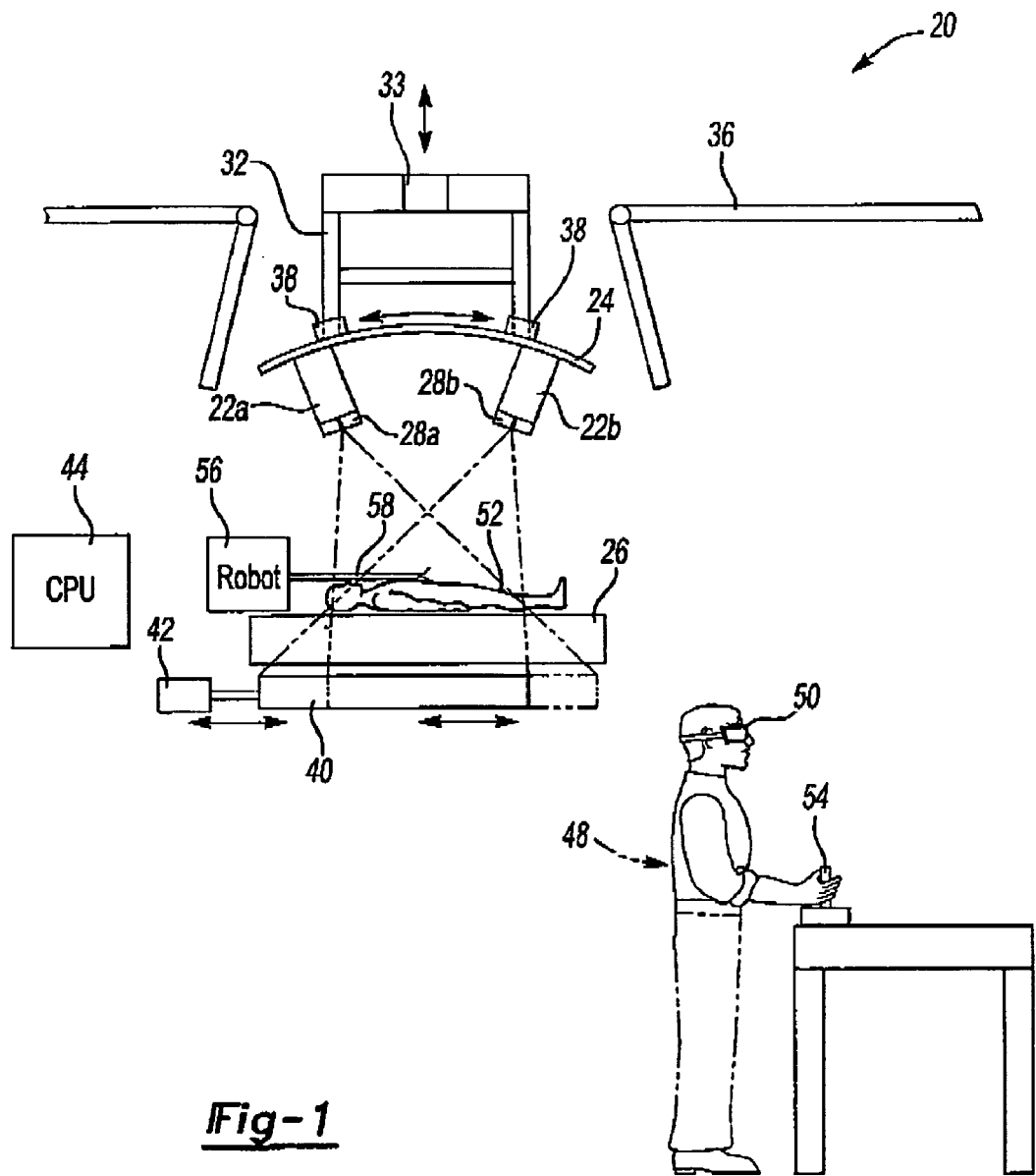
FIG. 1 illustrates a first embodiment of a surgical navigation and imaging system according to the present invention.

The present invention shown in FIG. 1 provides an imaging system 20 particularly useful for image-guided surgery, remotely-controlled robotic surgery or other applications where intra-operative imaging would be desired. Although potentially useful for other types of imaging systems, the present invention will be described with respect to an intra-operative CT scanning system 20.

Referring to FIG. 1, the imaging system 20 includes a pair of laterally offset sources 22a, 22b both mounted on a bracket 24 above a radiolucent operating table 26. The bracket 24 is mounted to a lift 32 that is powered by a motor 33 to extend and retract down from and into the ceiling 36 above the operating table 26. The bracket 24 is coupled to the lift 32 via motorized couplings 38 for selectively moving the bracket generally along an arcuate path. Alternatively, the bracket 24 may be mounted on a robotic arm.

The sources 22a, 22b may be cone-beam x-ray sources. Each of the sources 22a, 22b includes a video camera 28a, 28b, respectively. The video cameras 28a, 28b are positioned such that the field of view of the video image received by each video camera 28a, 28b substantially corresponds to the beam of x-rays emitted from the associated source 22a, 22b.

A detector 40 is mounted below the operating table 26 and is positioned to receive the x-ray beams frani the sources 22a, 22b. As shown in FIG. 1, if the detector 40 is not large enough to receive the entire beam from both of the sources 22a, 22b the detector 40 may be translated back and forth (e.g, by a computer-controlled motor or actuator 42) between a first position for receiving an x-ray beam from the first source 22a and a second position for receiving an x-ray beam from the second source 22b.

The system 20 further includes a computer 44 that is suitably programmed to control the functions of all of the devices described herein and to perform the image-processing described herein.

A surgeon 48 views a display, such as a goggle stereo display 50, producing images from the detector 40 and sources 22a, 22b of the region of interest of the patient 52. An input device 54, such as a computer input device with haptic feedback, or other remote surgical device, controls a surgical robot 56. The surgical robot 56 uses surgical tools 58 to perform surgery on the patient 52 based upon the input from the surgeon 48 on the input device 54. Remote surgery, surgical robots and haptic feedback surgical devices are all described and known in the art.

In use, the sources 22a, 22b alternately generate x-rays that pass through the patient 52 and are received as images by the detector 40. These images from slightly different angles are displayed simultaneously to the surgeon 48 on the stereo display 50 and continuously updated to provide a three-dimensional image to the surgeon 48. Based upon the three-dimensional image, the surgeon 48 controls the surgical robot 56 in the surgery using the input device 54. The surgeon 48 can also remotely control movement of the bracket 24 and sources 22a, 22b to change the perspective of the three-dimensional view. Additionally, the surgeon 48 can choose for the stereo display 50 to toggle between or dissolve between an outer, visible three-dimensional view provided by the cameras 28a, 28b and the stereo fluoroscopy provided by the sources 22a, 22b and detector 40. In this manner, the surgeon 48 can remotely control the location and orientation of the sources 22a, 22b while watching the video images from the cameras 28a, 28b and then switch to the stereo fluoroscopy view when the desired portion of the patient is located.

Other variations of the present invention include the use of a single source that could be moved between the two locations to provide the stereo view. The surgical robot 56 could be used to move the source(s).

Figure 2:
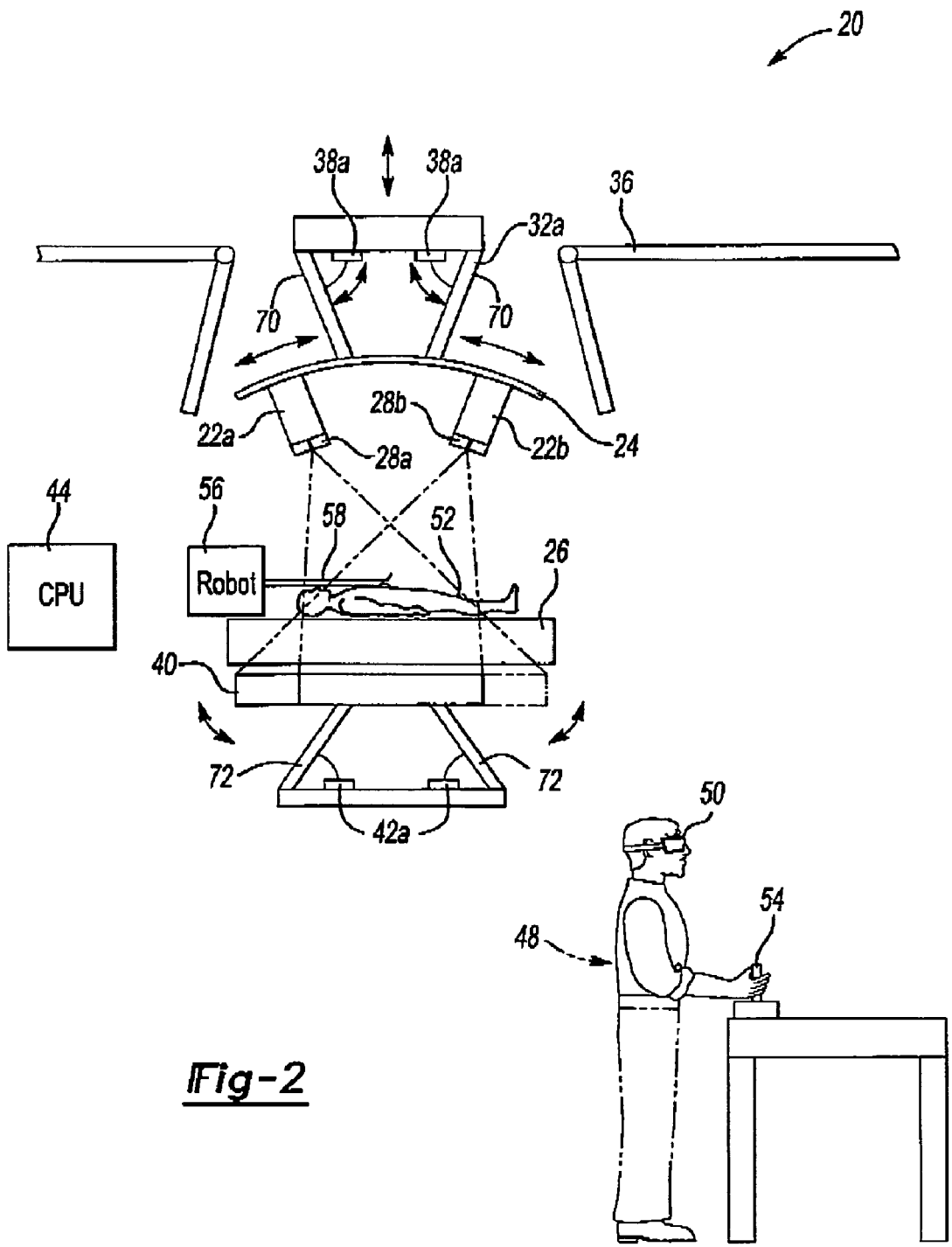
FIG. 2 illustrates a second embodiment of a surgical navigation and imaging system according to the present invention.

FIG. 2 illustrates a second embodiment of the imaging system 20 according to the present invention. If the sources 22a, 22b are rotated to change the viewing angle a sufficient degree, it may become necessary or desirable to rotate the detector 40 as well. In this embodiment, the bracket 24 holding the sources 22a, 22b and the detector 40 are mounted in four-bar linkages (shown only schematically in FIG. 2, not to scale). The bracket 24 is mounted to two links 70 acted upon by computer-controlled motors or actuators 38a. The detector 40 is similarly mounted to two links 72 controllably pivoted by computer-controlled motors or actuators 42a. This provides an economical way to provide for controlled movement of the sources 22a, 22b and detector 40 about known arcs.

By providing for movement about known arcs about the patient 52, the sources 22a, 22b and detector 40 can then additionally be used for computed tomography. If full angular range is provided (i.e. approximately 180 degrees), then a full CT scan can be performed by the system 20. Alternatively, limited angle tomography can be performed intraoperatively based upon data from a complete pre-operative CT scan. The limited angle tomography can be used during surgery to update the data from a pre-operative full and complete CT scan. In that case, the computer 44 can generate a three-dimensional model of the current state of the patient 52 and can computer-generate a "simulated" three-dimensional angle to the surgeon's stereo display 50 based upon the updated three-dimensional model. The simulated three-dimensional model would be integrated with the image-guided surgical system, such that the position and orientation of the surgical robot tool 58 would also be displayed on the stereo display 50.

In accordance with the provisions of the patent statutes and jurisprudence, exemplary configurations described above are considered to represent a preferred embodiment of the invention. However, it should be noted that the invention can be practiced otherwise than as specifically illustrated and described without departing from its spirit or scope. Alphanumeric identifiers in method steps are for the purpose of ease of reference in dependent claims and are not intended to signify a required sequence of performance, and unless otherwise explicitly stated, such sequence should not be inferred.

What is claimed is:

1. A surgical imaging system comprising:
   a first x-ray source at a first location above a patient support surface;
   a second x-ray source laterally spaced from the first x-ray source and above the patient support surface;
   an x-ray detector mounted below the patient support surface, the x-ray detector generating first x-ray images based upon x-rays from the first x-ray source and second x-ray images based upon x-rays from the second x-ray source, wherein the x-ray detector is movable between a first position where the x-ray detector receives x-rays from the first x-ray source and a second position where the x-ray detector receives x-rays from the second x-ray source
   an actuator for moving the x-ray detector relative to the first x-ray source and the second x-ray source from the first position to the second position and from the second position to the first position; and
   a first video camera mounted proximate the first x-ray source and a second video camera mounted proximate the second x-ray source, the first video camera generating first video images, the second video camera generating second video images.

2. The system of claim 1 further including a surgical robot operatively controlling a surgical tool in an area between the first x-ray source and the x-ray detector, and between the second x-ray source and the x-ray detector.

3. The system of claim 2 wherein the first video camera has a field of view similar to that of the first x-ray source and the second video camera has a field of view similar to that of the second x-ray source.

4. The system of claim 3 further including a stereo display displaying the first and second x-ray images.

5. The system of claim 4 wherein the stereo display selectively displays the first and second video images or the first and second x-ray images.

6. The system of claim 1 further including a stereo display displaying the first and second x-ray images.

7. The system of claim 1 wherein the first x-ray source alternates generating x-rays with the second x-ray source.

8. The system of claim 1 wherein the actuator moves the x-ray detector in a first direction from the first position to the second position and in a second direction, opposite the first direction, from the second position to the first position.

9. The system of claim 8 wherein the actuator moves the x-ray detector substantially linearly.

10. A surgical imaging system comprising:
    a first x-ray source at a first location above a patient support surface;
    a second x-ray source laterally spaced from the first x-ray source and above the patient support surface;
    an x-ray detector mounted below the patient support surface, the x-ray detector generating first x-ray images based upon x-rays from the first x-ray source and second x-ray images based upon x-rays from the second x-ray source, wherein the first x-ray source and the second x-ray source are mounted to move along an arc above the patient support surface; and
    a surgical robot operatively controlling a surgical tool in an area between the first x-ray source and the x-ray detector, and between the second x-ray source and the x-ray detector, the x-ray detector generating the first x-ray images and the second x-ray images while the surgical tool is between the first x-ray source and the x-ray detector and between the second x-ray source and the x-ray detector, respectively.

11. The system of claim 10 wherein the first x-ray source and the second x-ray source are mounted to four-bar linkages.

12. The system of claim 10 wherein the detector is mounted to move along an arc.

13. A surgical imaging system comprising:
    a first x-ray source at a first location above a patient support surface;
    a second x-ray source laterally spaced from the first x-ray source and above the patient support surface;
    an x-ray detector mounted below the patient support surface, the x-ray detector generating first x-ray images based upon x-rays from the first x-ray source and second x-ray images based upon x-rays from the second x-ray source;

an actuator moving the x-ray detector between a first position where the x-ray detector receives x-rays from the first x-ray source and a second position where the x-ray detector receives x-rays from the second x-ray source; and a surgical robot operatively controlling a surgical tool in an area between the first x-ray source and the x-ray detector, and between the second x-ray source and the x-ray detector, the x-ray detector generating the first x-ray images and the second x-ray images while the surgical tool is between the first x-ray source and the x-ray detector and between the second x-ray source and the x-ray detector, respectively.

* * * * *